(12) United States Patent
Block et al.

(10) Patent No.: US 10,864,042 B2
(45) Date of Patent: Dec. 15, 2020

(54) OPTICAL ASSEMBLY FOR LASER GENERATOR

(71) Applicant: KONINKLIJKE PHILIPS N.V., Eindhoven (NL)

(72) Inventors: Gabriel Block, Colorado Springs, CO (US); Kenneth P. Grace, Woodland Park, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 297 days.

(21) Appl. No.: 15/900,258

(22) Filed: Feb. 20, 2018

(65) Prior Publication Data

US 2019/0254746 A1   Aug. 22, 2019

(51) Int. Cl.
*A61B 18/24* (2006.01)
*G02B 27/09* (2006.01)
*A61B 18/20* (2006.01)

(52) U.S. Cl.
CPC ............ *A61B 18/24* (2013.01); *A61B 18/203* (2013.01); *G02B 27/0955* (2013.01); *G02B 27/0972* (2013.01); *G02B 27/0977* (2013.01); *A61B 2018/20553* (2017.05)

(58) Field of Classification Search
CPC .................. A61B 18/24; A61B 18/203; A61B 2018/20553; G02B 27/0972; G02B 27/0977

See application file for complete search history.

(56) References Cited

U.S. PATENT DOCUMENTS

| | | | | |
|---|---|---|---|---|
| 5,383,199 A | * | 1/1995 | Laudenslager | A61B 18/20 372/25 |
| 2002/0002367 A1 | | 1/2002 | Tankovich | |
| 2012/0143176 A1 | * | 6/2012 | Ryan | A61B 18/24 606/3 |
| 2015/0372446 A1 | * | 12/2015 | Chuang | H01S 3/005 372/25 |
| 2018/0223874 A1 | * | 8/2018 | Maruyama | F04D 29/668 |

FOREIGN PATENT DOCUMENTS

| | | |
|---|---|---|
| DE | 19508100 A1 | 8/1996 |
| EP | 0362466 A2 | 4/1990 |
| EP | 3281598 A1 | 2/2018 |
| JP | 2001111147 A | 4/2001 |

* cited by examiner

*Primary Examiner* — Lynsey C Eiseman
*Assistant Examiner* — Amanda L Steinberg

(57) ABSTRACT

Methods and devices for an optical assembly for a laser generator comprise: a laser source producing a first beam of light and an optical assembly. The optical assembly comprises a prism. The prism has a bottom surface configured to receive a first beam at an incoming angle of incidence relative to a first surface normal, and a hypotenuse surface configured to transmit, at an exit angle relative to a second surface normal, a second beam having a second aspect ratio. The optical assembly further comprises a plano-convex lens configured to transmit the second beam to a coupler. The coupler comprises a first coupling plane at a first distance from the plano-convex lens and a second coupling plane at a second distance from the plano-convex lens. The combination of the prism and the plano-convex lens is configured to change the beam divergence, so that the first coupling plane has a third aspect ratio and the second coupling plane has a fourth aspect ratio.

20 Claims, 12 Drawing Sheets

OPTICAL ASSEMBLY FOR LASER GENERATOR

FIELD OF THE DISCLOSURE

The present disclosure relates generally to devices, methods and systems for laser generators, and more specifically, to laser generators having an optical assembly, which allows fiber optic catheters to couple to laser generators while delivering laser beams with a consistent beam aspect ratio and beam divergence characteristics.

BACKGROUND

When performing a laser atherectomy procedure in a patient's vasculature and utilizing a disposable fiber optic catheter, the catheter is typically coupled to a laser generator, such as the CVX-300™ excimer laser system, which is manufactured by The Spectranetics Corporation, Colorado Springs, Colo., USA. Different laser generators generally produce different laser beams having distinct aspect ratios and beam divergence characteristics. As such, the laser beam produced by one laser generator may have size and divergence characteristics that vary significantly from another laser generator due to electrode width and spacing within the laser cavity. The length of the cavity and the radius of curvature of the laser cavity optics in the laser generator systems also contribute to the location of the laser beam waist and divergence. A need exists to optically tailor laser a generator system's beam characteristics to make disposable fiber optic catheters compatible with multiple laser generator systems.

SUMMARY

Accordingly, there is a need for a device, method and/or laser generator system that includes an optical assembly device, which has the ability to tailor the aspect ratio of a beam produced by one laser generator so that a disposable fiber optic catheter has the capability to couple to multiple laser generator systems. The present disclosure discusses a method, device and system for laser generators that satisfies such needs.

A laser generator device in accordance with this disclosure may include a laser source producing a first beam of light having a first aspect ratio and an optical assembly. The optical assembly may comprise a prism having a surface configured to receive the first beam at an incoming angle of incidence relative to a first surface normal and an additional surface configured to transmit, at an exit angle relative to a second surface normal, a second beam having a second aspect ratio; and, a lens configured to transmit the second beam to a coupler. The coupler may comprise a first coupling plane at a first distance from the lens, and a second coupling plane at a second distance from the plano-convex lens. The combination of the prism and the lens may be configured to change the beam divergence, so that the first coupling plane has a third aspect ratio and the second coupling plane has a fourth aspect ratio.

The device according to the previous paragraph may also or alternatively include wherein the prism is a wedge prism.

The device according to any of the previous paragraphs may also or alternatively include wherein the prism is a right angle wedge prism.

The device according to any of the previous paragraphs may also or alternatively include wherein the optical assembly further comprises a first sensor and a mirror disposed at an angle between the laser source and the prism, wherein the mirror reflects the first beam onto the prism, wherein the mirror further transmits at least a portion of the first beam to the first sensor, the first sensor configured to measure a first density of the first beam, wherein the mirror transmits about one percent of the first beam to the first sensor.

The device according to any of the previous paragraphs may also or alternatively include wherein the optical assembly further comprises a second sensor configured to measure a second energy of the second beam.

The device according to any of the previous paragraphs may also or alternatively include wherein the hypotenuse surface of the prism includes a coating configured to reflect at least a portion of the second beam to the second sensor.

The device according to any of the previous paragraphs may also or alternatively include wherein the coating reflects about two percent of the second beam to the second sensor.

The device according to any of the previous paragraphs may also or alternatively include wherein the optical assembly further comprises a third sensor configured to calibrate the laser source to a selected catheter, the catheter coupled to the optical assembly via the coupler.

The device according to any of the previous paragraphs may also or alternatively include a microprocessor executable controller and a safety shutter, wherein the safety shutter is disposed between the prism and the piano-convex lens, wherein the microprocessor executable controller closes the safety shutter upon receipt of a fault signal.

The device according to any of the previous paragraphs may also or alternatively include wherein the prism comprises fused silica.

The device according to any of the previous paragraphs may also or alternatively include wherein the optical assembly further comprises an attenuator disposed between the laser source and the prism, wherein the attenuator is configured to adjust the first energy of the first beam.

The device according to any of the previous paragraphs may also or alternatively include a microprocessor executable controller coupled to the attenuator, wherein the microprocessor executable controller adjusts the first energy of the first beam with the attenuator based upon the second energy of the second beam measured by the second sensor.

The device according to any of the previous paragraphs may also or alternatively include wherein the microprocessor executable controller adjusts the first energy of the first beam measured by a first sensor with the attenuator based upon the second energy of the second beam measured by a second sensor.

The device according to any of the previous paragraphs may also or alternatively include wherein the optical assembly further comprises a mirror that reflects the first beam onto the prism, wherein the mirror further transmits at least a portion of the first beam to the first sensor.

The device according to any of the previous paragraphs may also or alternatively include wherein the prism comprises: a bottom incident face configured to receive the first beam at an angle of 15 to 30 degrees off normal to the bottom incident face, the first beam having a first width and a first height; a side face connected to the bottom incident face by an edge at an angle of 90 degrees; and, a hypotenuse exit face connecting the bottom incident face and the side face, the hypotenuse exit face configured to emit the second beam at an angle of 50 to 70 degrees off normal to the hypotenuse exit face, the second beam having a second width and a second height, wherein the second width is less than the first width, and wherein the second height is the same or equal to the first height.

The device according to any of the previous paragraphs may also or alternatively include wherein the prism is configured to receive the first beam along an optical path and to affect at least one of beam size, beam divergence, beam long axis, and beam aspect ratio.

The device according to any of the previous paragraphs may also or alternatively include wherein the prism comprises a bottom surface, and the surface is the bottom surface.

The device according to any of the previous paragraphs may also or alternatively include wherein the prism comprises a hypotenuse surface, and the additional surface is the hypotenuse surface.

The device according to any of the previous paragraphs may also or alternatively include wherein lens is a plano-convex lens.

A system in accordance with this disclosure may include a laser generator and a catheter comprising a plurality of optical fibers, wherein the catheter comprises a proximal end and a distal end, wherein the proximal end is coupled to the coupler of the laser generator. The laser generator may comprise a laser source producing a first beam of light and an optical assembly. The optical assembly may comprise a prism and, a lens configured to transmit the second beam to a coupler. The prism may have a surface configured to receive the first beam at an incoming angle of incidence relative to a first surface normal, and an additional surface configured to transmit, at an exit angle relative to a second surface normal, a second beam having a second aspect ratio. The coupler may comprise a first coupling plane at a first distance from the lens, and a second coupling plane at a second distance from the lens. The combination of the prism and the lens may be configured to change the beam divergence, so that the first coupling plane has a third aspect ratio and the second coupling plane has a fourth aspect ratio.

The method of using the laser generator device or system, as detailed above, may include: providing a catheter comprising a plurality of optical fibers, wherein the catheter comprises a proximal end and a distal end; coupling the proximal end of the catheter to the coupler of the laser generator; inserting the distal end of the catheter into a patient's vasculature; and activating the laser generator.

The method may include wherein the laser generator is activated by a footswitch.

The method may also or alternatively include sensing a first energy of the first beam via a first sensor, sensing a second energy of the second beam via a second sensor, and calibrating the second energy to the provided catheter via a third sensor.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1A:
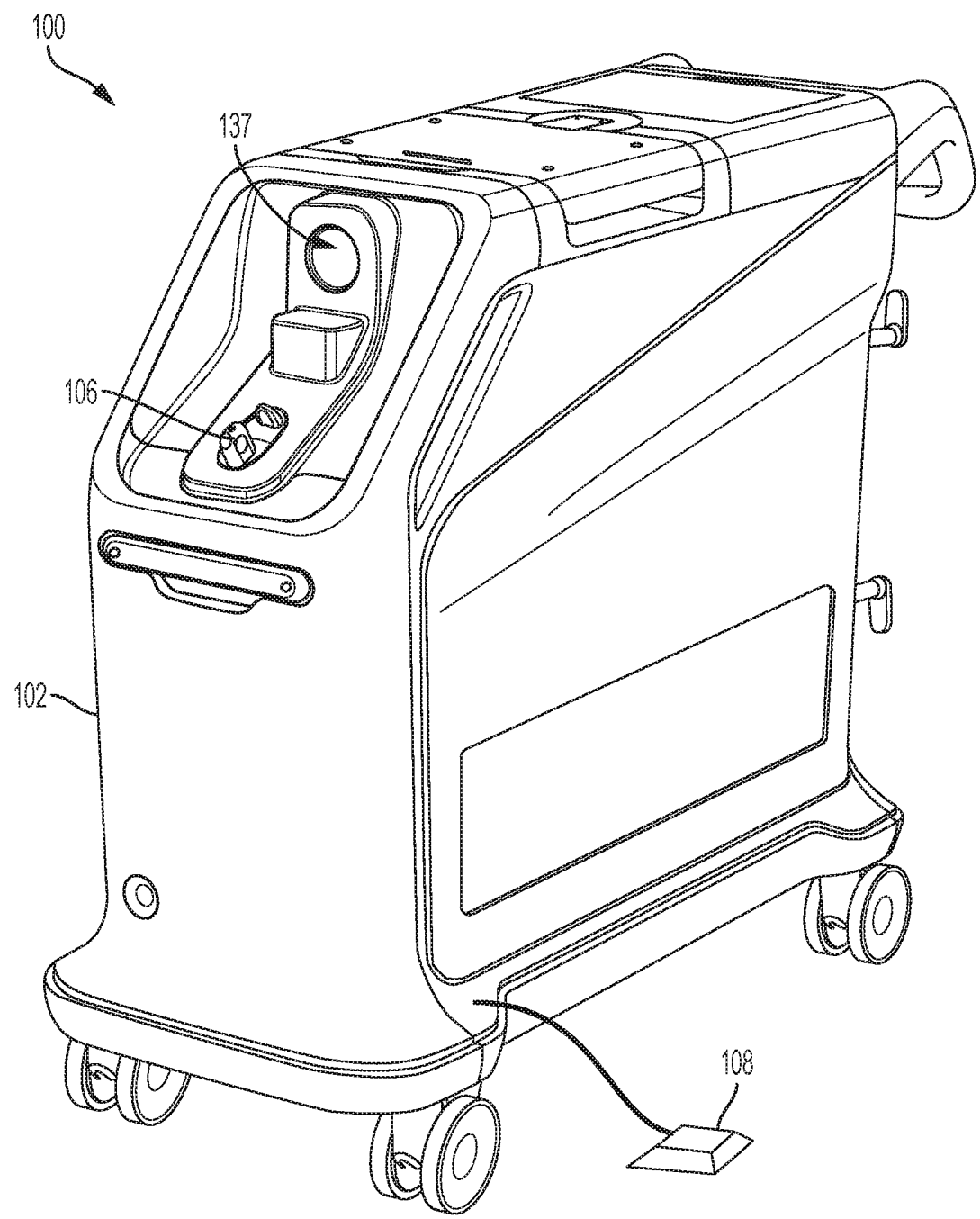
FIG. 1A is a perspective view of an embodiment of a laser generator of the present disclosure.

Embodiments according to this disclosure include a laser generator having an optical assembly that provides a beam having certain optical characteristics at a coupler to match the optical characteristics of a beam produced by a different laser generator or source. FIG. 1A depicts a laser generator 100 having a laser generator housing 102 and a catheter coupler 106. Laser generator 100 may further include a switch unit located remotely from the housing such as a switch controller 108, e.g. a footswitch. In embodiments, switch controller 108 may be wired or connected to the housing via a tether, for example, or alternatively switch controller 108 may be wireless. Laser generator 100 further includes a calibration sensor 137 to calibrate the laser according to a selected catheter.

Figure 1B:
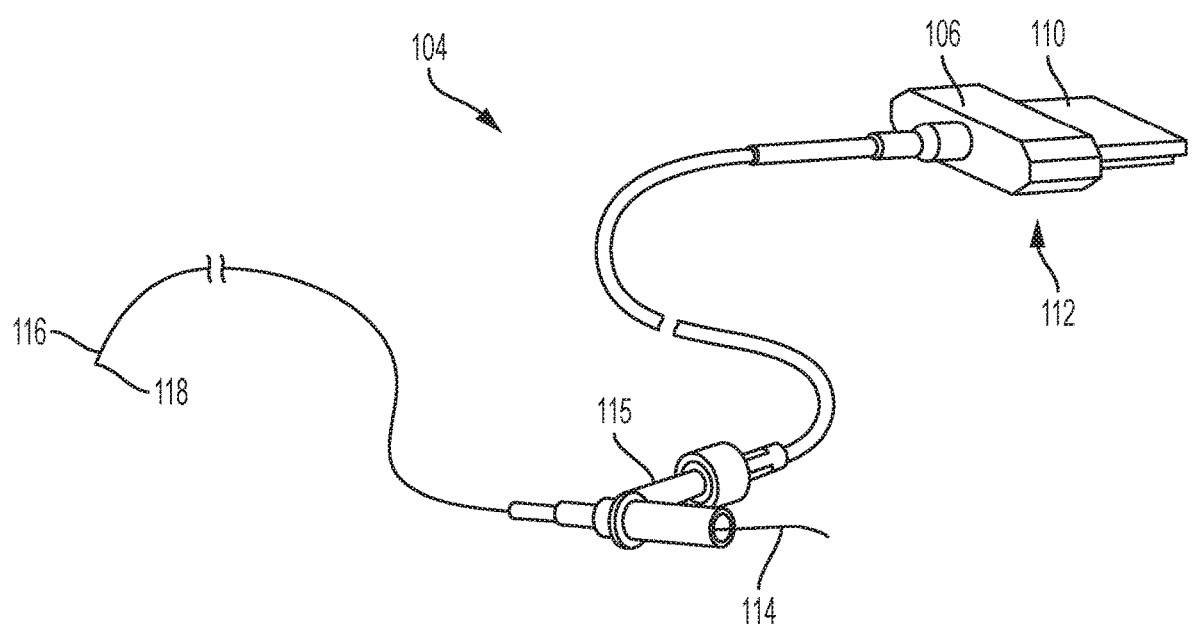
FIG. 1B is a perspective view of an embodiment of a laser catheter or fiber optic catheter of the present disclosure.

FIG. 1B depicts a non-limiting example of a laser catheter 104 suitable for coupling to laser generator 100 at catheter coupler 106. For example, laser catheter 104 includes a proximal end 110 and a distal end 116. The catheter coupler 106 is disposed at catheter proximal end 110. Catheter coupler 106 includes a plurality of optical fibers 112, which may be arranged in one or more sets of optical fibers 112, wherein the optical fibers 112 are disposed throughout the length of the laser catheter 104, including being housed within coupler 106 and exposed at the distal tip 118 of the distal end 116. Laser catheter 104 may also include a T or Y connector 115, wherein the connector 115 has an entry port for a guidewire 114 to be inserted therein. The laser catheter 104 may further include a lumen extending from the connector 115 to the distal end 116 of catheter 104 at distal tip 118, thereby allowing the guidewire to be inserted through the catheter 104.

Figure 2:
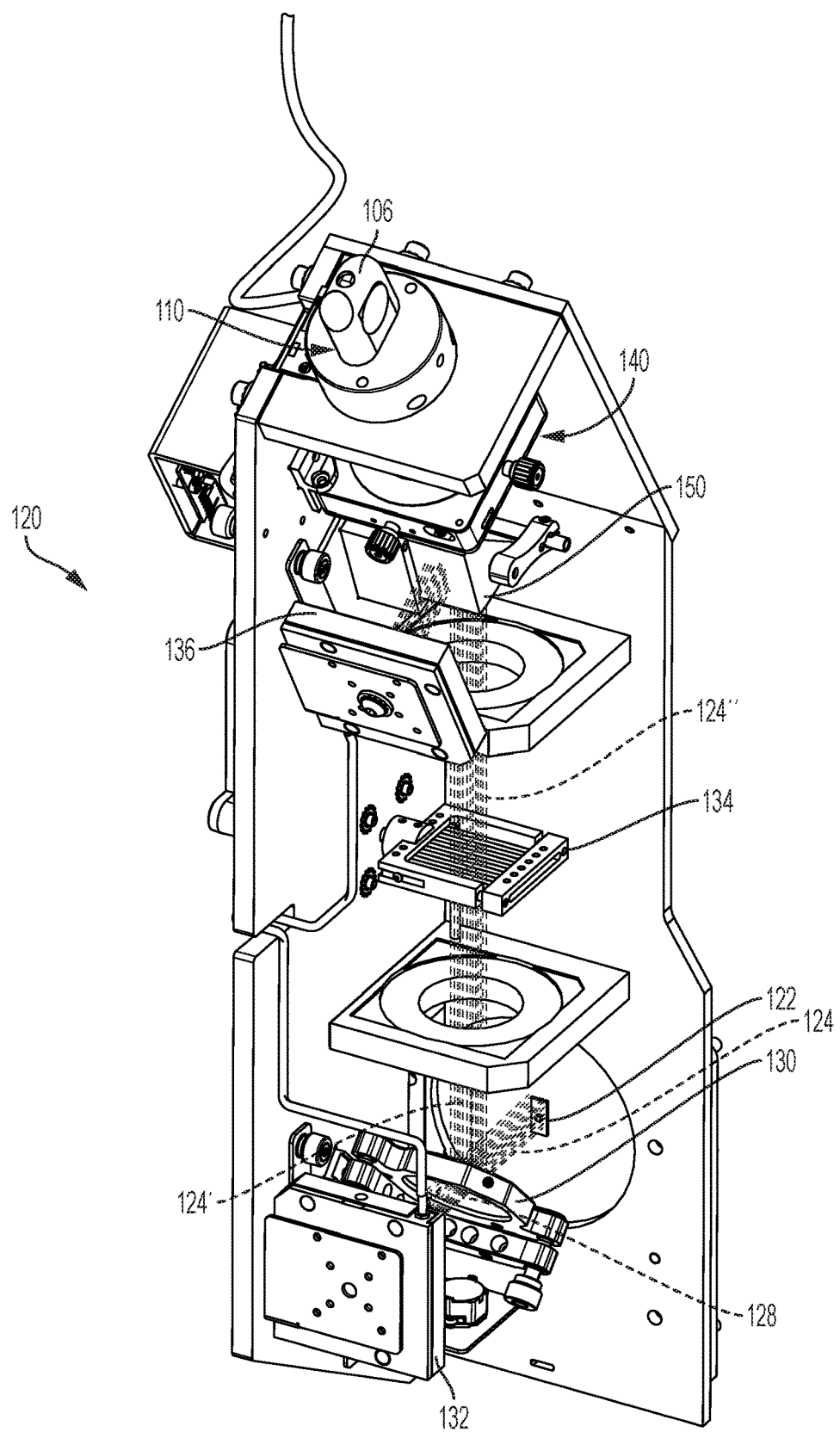
FIG. 2 is a perspective view of an embodiment of an optical assembly of the present disclosure.
Figure 3:
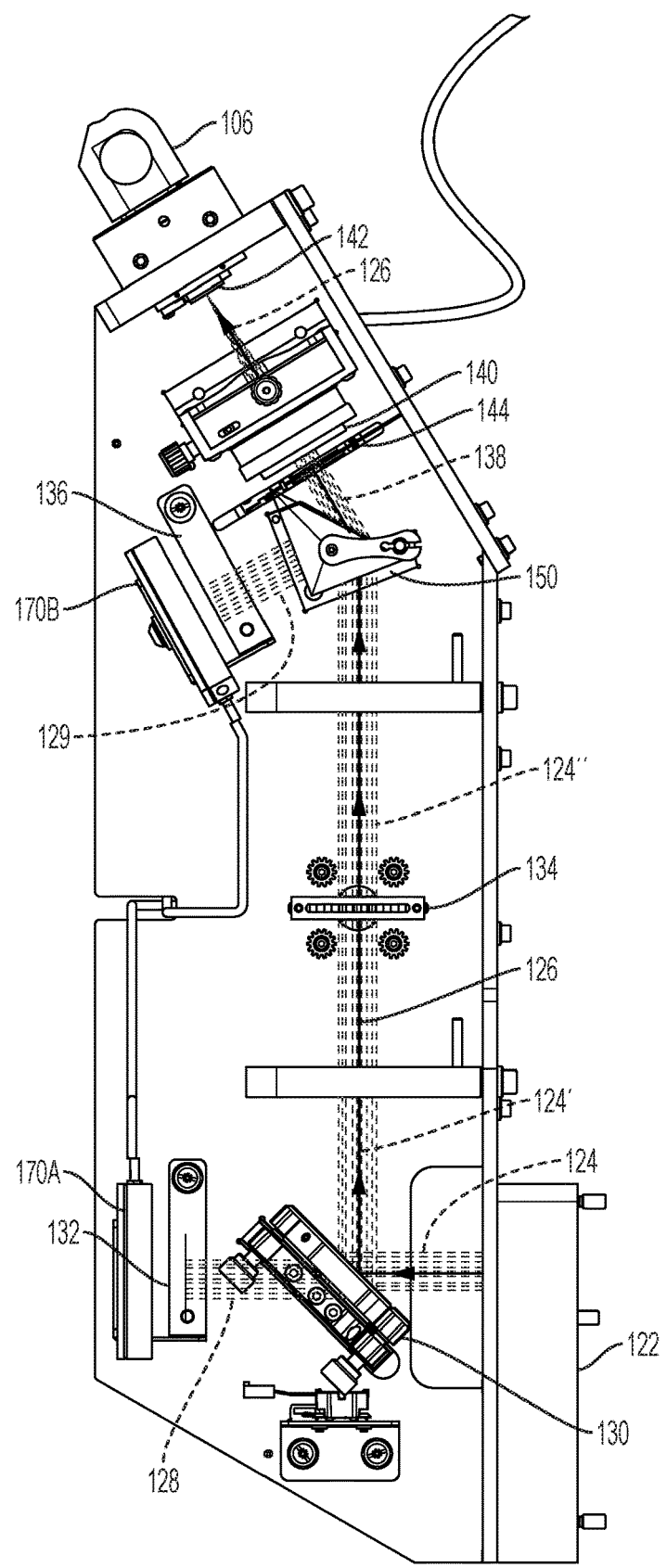
FIG. 3 is a side view of the optical assembly depicted in FIG. 2.

Within housing 102, the laser generator 100 includes optical assembly 120 and a laser source 122 as illustrated in perspective view FIG. 2 and in side view FIG. 3. Optical assembly 120 is coupled to catheter 104 via coupler 106. Optical assembly 120 is also coupled to laser source 122, thereby providing an optical pathway 126 from the laser source 122 to the coupler 106.

Referring to FIG. 2 and FIG. 3, the optical assembly 120 may include a mirror 130, an energy sensor 132, an attenuator 134, a prism 150, a prism energy sensor 136, and a plano-convex focusing lens 140. The laser source 122, the mirror 130 and the sensor 132 are aligned in a first plane, such as a lateral plane. The mirror 130, the attenuator 134 and the prism 150 are aligned in second plane, such as a vertical plane. The prism 150, plano-convex focusing lens 140, and the fiber coupler 142 of catheter coupler 106 are aligned in another plane, such as a vertically offset plate. Additionally, the first plane and the second plane may be offset from one another at an angle between 1 degree and 179 degrees, and preferably at an angle between 45 degrees and 135 degrees, and more preferably between 60 degrees and 120 degrees, and even more preferably about 90 degrees. Furthermore, the second plane and the other plane may be offset from one another at an angle between 1 degree and 179 degrees (e.g., 2°, 3°, 4°, 5°, . . . , 10°, . . . , 15°, . . . , 30°, . . . , 45°, . . . , 60°, . . . , 75°, . . . , 90°, . . . , 105°, . . . , 120°, . . . , 135°, . . . , 150°, . . . , 165°, . . . , 170°, . . . , 75°, . . . , 178°).

Generally prism optical elements are recited herein for refracting, bending, deviating, or compressing the first beam in at least one axis. However, it is contemplated that any appropriate optical element may be used for refracting, bending, deviating, or compressing the first beam in at least one axis such as non-limiting examples of a wedged optical element, a circular optical element, and a multi-sided optical element such as a Fresnel prism having segmented flat, prism faces.

Optical assembly 120 receives laser beam 124 from laser source 122 along optical pathway 126, which extends from the laser source 122 to coupler 106. Optical pathway 126 is illustrated by the arrows on FIG. 3 to indicate the laser beam direction of travel from the laser source to the catheter coupler. Optical pathway 126 originates at laser source 122 extending in a lateral plane to mirror 130, changing direction to a vertical plane to prism 150. At prism 150, optical pathway 126 changes direction to a vertically offset plane to fiber coupler 142.

Laser beam 124 has a first beam aspect ratio. An aspect ratio may be calculated as a ratio of a beam's width (w) to a beam's height (h), which can be expressed as w:h. Alternatively, an aspect ratio may be calculated as a ratio of a beam's height (h) to a beam's width (w), which can be expressed as h:w. As such, the first aspect ratio may be calculated as the ratio of a first beam width ($w_1$) to a first beam height ($h_1$) and may be written as $w_1$:$h_1$ or vice versa. In embodiments, laser beam 124 is rectangular in cross-section and has a first beam width ($w_1$) and a first beam height ($h_1$).

Laser beam 124 is directed from the laser source 122 to the mirror 130, and the mirror 130 reflects laser beam 124' toward attenuator 134, which is discussed in more detail below. The prime designation for laser beam 124' denotes that laser beam 124' has the same aspect ratio as laser beam 124 but may differ in energy and/or direction of travel. Generally, energy is measured in millijoules (mJ). Alternatively, in accordance with the present disclosure, power may be measured as with continuous wave (CW) lasers or pulse lasers. The mirror 130 is offset at an angle (θ) (e.g., 45 degrees) from the pathway from the laser source 122 to the mirror 130. The mirror 130 may be configured to allow at least a portion of laser beam 124, the portion referred to as laser beam 128 as in FIGS. 2 and 3, to be transmitted through mirror 130. For example, mirror 130 may transmit about between one and five percent of the energy of the beam 124 to the sensor 132, which is in-line or along the same plane as the mirror 130 and the laser source 122, and the mirror 130 reflects about between ninety-five and ninety-nine percent of the energy of the beam towards the attenuator 134. If the mirror is configured as such, the sensor 132 measures the energy of the laser beam exiting the laser source 122, and the sensor 132 transmits the energy measurement to the controller 520, which is discussed in more detail below. If the sensor 132 is omitted from the optical assembly 120, then the mirror 130 may be configured to reflect about all (i.e., 100 percent) of the energy of the laser beam 124' towards the attenuator 134.

Regardless of the percentage of the laser beam's energy that is reflected by the mirror 130, the attenuator 134 receives beam 124' having an aspect ratio that is the same as the first aspect ratio of beam 124 because the mirror 130 does not alter the first aspect ratio produced by the laser source 122. The attenuator is designed or configured to attenuate or reduce the energy of the beam 124' passing there through, if so desired. For example, the attenuator 134 may have multiple positions or settings such that it is adjustable and interactive with input/output ports and/or components. Attenuator 134 may be completely open or completely closed. When the attenuator 134 is in the completely open position, the attenuator does not significantly reduce any of the laser beam's energy. For example, there may a 10% loss (or 5% loss or 3% loss) of energy when in the open position. When the attenuator 134 is in the completely closed position, the attenuator 134 reduces all of the laser beam's energy. In embodiments, attenuator 134 may be partially open or partially closed to reduce the energy intensity of beam 124' passing there through to provide beam 124". The double prime designation for laser beam 124" denotes that laser beam 124" has the same aspect ratio as laser beam 124' and laser beam 124 but may differ in energy and/or direction of travel. That is, when the attenuator 134 is in the partially open or partially closed position, the attenuator 134 reduces a portion or percentage of the beam's energy. Regardless of the position of the attenuator and regardless whether none or a portion of the laser beam's energy is reduced, the attenuator does not alter the laser beam's aspect ratio. Beam 124" has the same aspect ratio of beam 124 and beam 124'. As such, the aspect ratio of the laser beam 124" exiting the attenuator 134 is the same as the first beam aspect ratio.

Figure 4A:
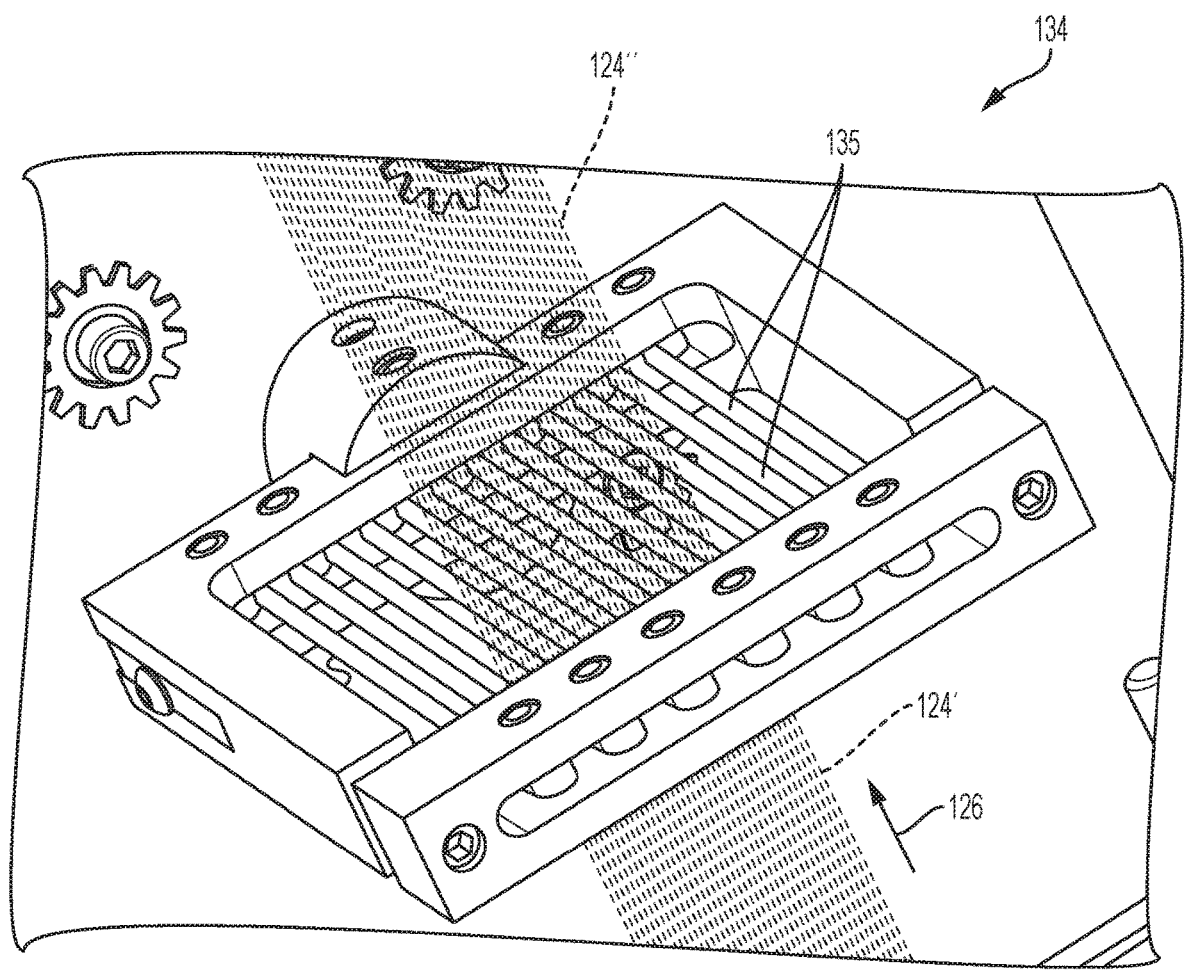
FIG. 4A is a perspective view of an attenuator of the optical assembly depicted in FIG. 2.
Figure 4B:
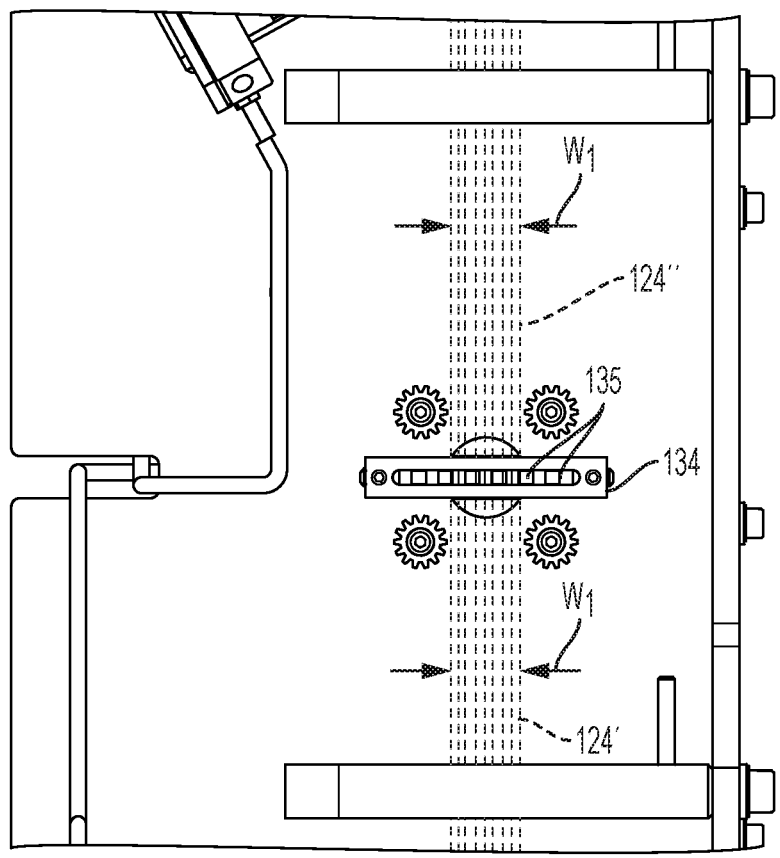
FIG. 4B is an enlarged side view of the attenuator of the optical assembly depicted in FIG. 3.
Figure 8:
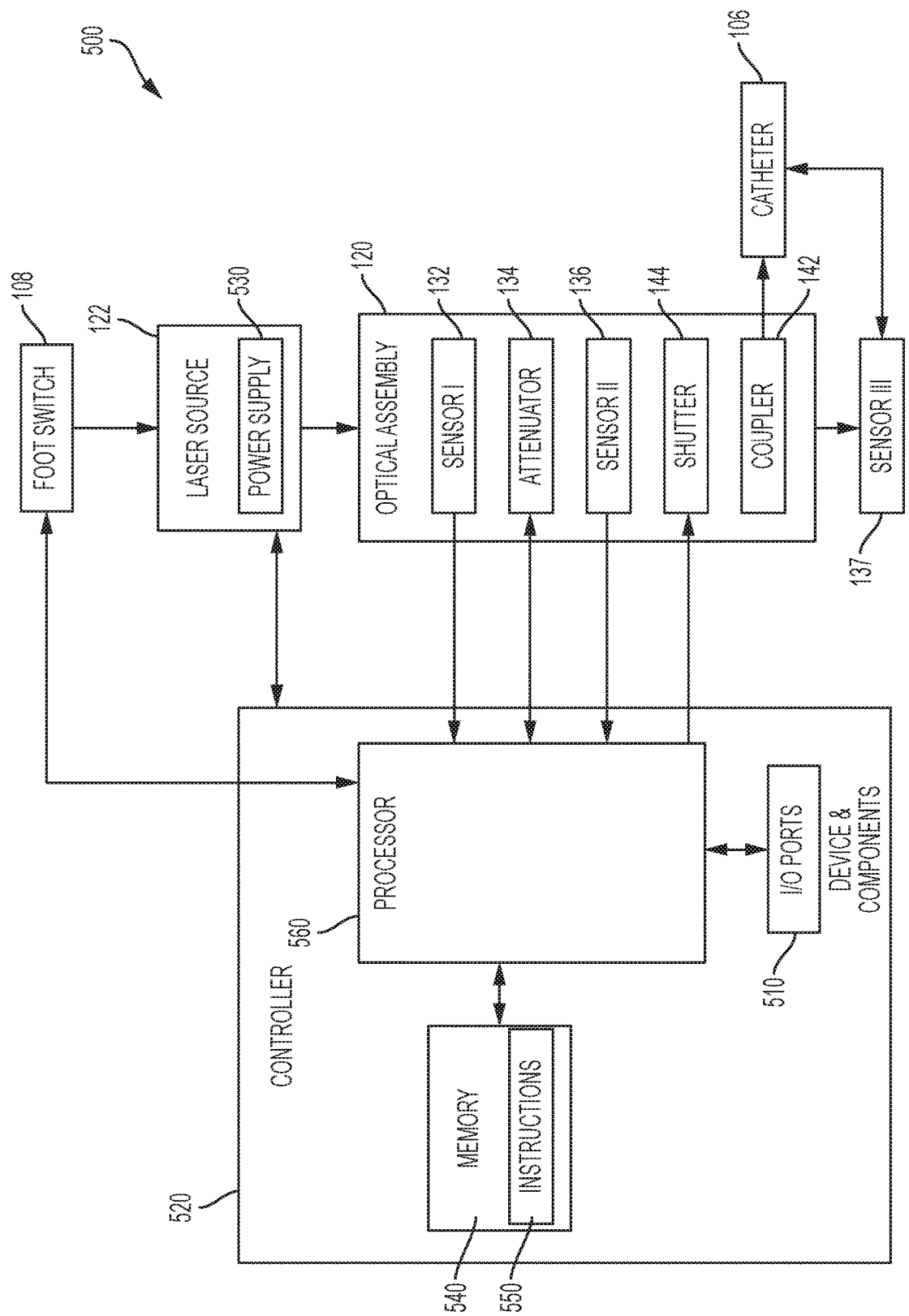
FIG. 8 is a block diagram of a system of the present disclosure.

FIG. 4A depicts a perspective view of an example of one type of attenuator 134 that may be used with optical assembly 120 illustrated in FIG. 3. Attenuator 134 includes louvers 135 that are oriented in the direction of optical pathway 126 in a first or open position to allow beam 124" to pass through with full beam density, the same beam density as for beam 124'. Louvers 135 may be rotated to at least partially decrease beam intensity without affecting beam width $w_1$. FIG. 4B depicts an enlarged side view of the attenuator of the optical assembly depicted in FIG. 3. Beam width $w_1$ is maintained and unchanged passing through attenuator 134. Louvers may be controlled by a stepper motor with encoder software for accurately adjusting beam energy by rotating the louvers 135, which are aligned vertically at a first or open position, to rotate partially or fully horizontally to another or closed position. In an open position, the louvers do not affect beam energy as discussed. By at least partially closing the louvers, the beam energy is lowered without affecting beam size, width, or aspect ratio. For example the beam energy of beam 124" may be lower than the beam energy of beam 124'. The stepper motor with encoder software is controllable via a microprocessor executable controller (refer to controller 520 as illustrated in FIG. 8).

Figure 5A:
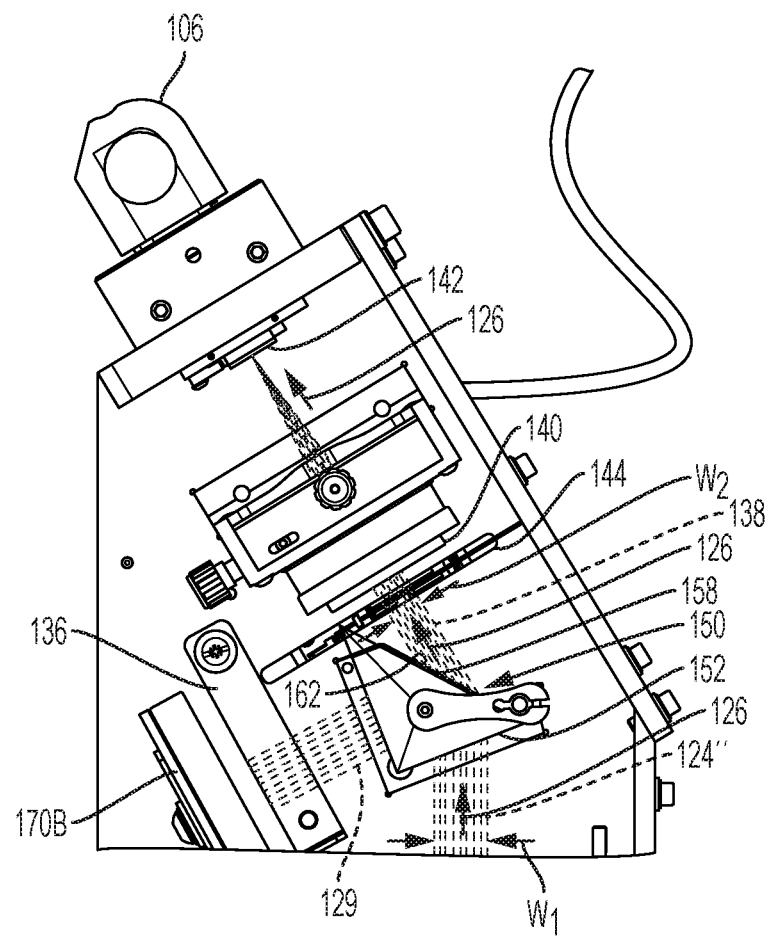
FIG. 5A is an enlarged side view of the prism and prism energy sensor of the optical assembly depicted in FIG. 3.
Figure 5B:
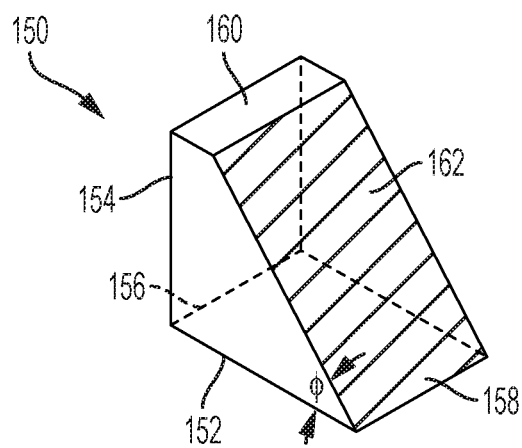
FIG. 5B is a perspective view of the prism depicted in FIG. 5A.
Figure 5C:
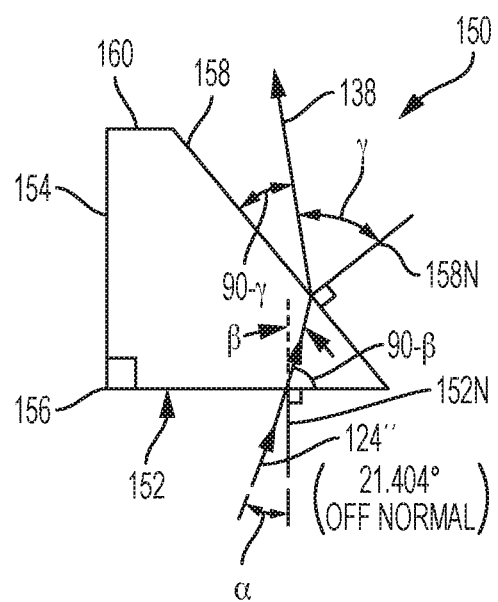
FIG. 5C is a two-dimensional view of the ray paths, into, through and from the prism depicted in FIG. 5A.

Referring to FIGS. 5A-5C, beam 124", traveling further along optical pathway 126, is then incident upon prism 150. As depicted in side view FIG. 3, incoming beam 124", having a first aspect ratio, enters prism 150 and passes through prism 150. Beam 124" then exits the prism as beam 138, having a second aspect ratio, wherein the first aspect ratio is different than the second aspect ratio. In other words, rather than assigning the prime designation as for laser beams 124, 124', and 124", all having the same aspect ratio, laser beam 138, which represents the laser beam as it exits the prism is denoted with a new element number 138, because laser beam 138 has an aspect ratio different from laser beam 124 (also 124' and 124"). In embodiments, the second aspect ratio is less than the first aspect ratio. In embodiments, beam 138 has a second width $w_2$, wherein the second width $w_2$ is less than the first width $w_1$. In an example shown in FIG. 5A, beam 124" has width $w_1$ and enters prism 150, which then exits prism 150 as beam 138. Beam 138 has width $w_2$, wherein $w_2$ is less than $w_1$.

Additionally, at least a portion of laser beam 138 at the exiting surface, depicted as beam 129 in FIG. 5A, may be reflected by a coating 162 applied to the exiting or hypotenuse surface 158 of the prism 150. In other words, beam 129 may be directed toward and through side surface 154 of the prism 150 and to energy sensor 136, where prism energy or a second energy is determined. Energy sensor 136 may send a corresponding signal to the microprocessor executable controller via component 170B. For example, the coating 162 may be comprised of any material suitable for reflecting at least a portion of beam 138 exiting surface 158 of prism 150. The coating may be designed to reflect any desired energy to direct toward sensor 136. In embodiments, coating 162 has a thickness designed to maintain maximum throughput while directing the desired energy percentage to sensor 136. Coating 162 may reflect about between one and five percent of the energy of the beam 138 to the sensor 136, which is in-line or along the same plane as the prism 150, and prism 150 having coating 162 transmits about between ninety-five and ninety-nine percent of the energy of the beam towards the plano-convex focusing lens 140. If the coating 162 is configured as such, the sensor 136 measures the energy of the laser beam 138 exiting the prism 150, and the sensor 136 transmits the energy measurement to the controller 520, which is discussed in more detail below. If the sensor 136 is omitted from the optical assembly 120, then the prism 150 may be configured to transmit about all (i.e., 100 percent) of the energy of the laser beam 138 towards the plano-convex focusing lens 140.

The prism 150 of FIG. 5A, is shown in detail in FIGS. 5B and 5C. In embodiments, prism 150 is a wedge prism. A prism may be a transparent optical element capable of refracting light and may include one or more surfaces, which may or may not be polished. One type of prism may be a wedge prism, which may have two surfaces (which could be flat) and offset from one another. Furthermore, prism 150 may be a right angle wedge prism. Prism 150, shown in perspective in FIG. 5B, has a bottom surface 152, to which beam 124" may be incident. A side surface 154 is connected to the bottom surface by an edge 156. In embodiments, edge 156 connects surfaces 152 and 154, which are at an angle of 90 degrees in comparison to one another. A hypotenuse surface 158 connects the bottom surface 152 and the side surface 154 (at chamfer 160 as shown) or may alternatively connect surfaces 154 and 158 at an edge. Chamfer 160 may be used, for example, to save space in the optical assembly cavity and does not affect beam characteristics, because chamfer 160 is not in the optical pathway 126. Bottom surface 152 is connected to the hypotenuse surface 158 at an angle (ϕ), which may be any degree between 1 degree and 90 degrees, and possibly between 15 degrees and 75 degrees, and possibly between 30 degrees and 60 degrees, and potentially between 40 degrees and 50 degrees, and between about 45 degrees and 50 degrees.

Prism 150 may be made of any suitable material having the desired optical properties, such as index of refraction, for refracting laser beams having varying wavelengths to accommodate multiple laser generator systems. The index of refraction value (n) provides a quantitative expression of the optical density of a given medium. Materials of different indices or refraction increase or decrease the dispersion (rate in which light is angularly deviated and/or compressed) for a desired wavelength of light. Suitable materials include silica or calcium fluoride. In embodiments, prism 150 comprises a material having an index of refraction (n) equal to from about 1.4 to about 1.5. In embodiments, prism 150 comprises fused silica having an index of refraction (n) equal to 1.458 for a laser generator system that produces a laser beam with a wavelength of 308 nm. An example prism material suitable in the present disclosure may be chosen from Corning HPFS® 7980 (Corning Inc., Corning, N.Y. 14831, USA), Dynasil 1103 (Dynasil Corporation, Newton, Mass. 02458, USA), and Suprasil® 2 (Heraeus Quarzglas GmbH & Co. KG, 63450 Hanau, Germany).

The prism 150 has an index of refraction (n) and is oriented to not only alter the optical pathway 126, but the prism may be oriented within the optical pathway 126 in such a way as to refract the laser beam in order to achieve certain beam characteristics. According to the configuration of the prism 150, wherein the incident and exiting surfaces (surfaces 152 and 158) are angularly offset from one another—not parallel to one another. As depicted in FIG. 5C, there is an axis 152N, which is normal (ninety degrees) to the bottom surface 152, and there is an axis 158N, which is normal to the hypotenuse surface 158.

Bottom surface 152 receive beam 124" at an angle ($\alpha$) with respect to axis 152N and at an angle 90° less angle ($\alpha$) with respect to bottom surface 152. Angle (a) may be zero degrees, thereby indicating that the bottom surface receives beam 124" from a direction along normal axis line 152N. Alternatively, the beam 124" may be directed at the bottom surface 152 at an angle ($\alpha$) or angularly offset from normal axis line 152N. If Beam 124" is received at an angle ($\alpha$) offset from normal 152N, the angle ($\alpha$) may be from about 1 degrees to about 89 degrees, and potentially from about 5 degrees to about 75 degrees, and possibly from about 10 degrees to about 60 degrees, and conceivably from about 15 degrees to about 45 degrees, and even 20 degrees to about 30 degrees, and maybe even about 20 degrees to about 25 degrees, and possibly even about 21.404 degrees.

Based upon the prism's index of refraction (n), the prism 150 may deflect beam 124" within the prism 150 at an angle ($\beta$) with respect to axis 152N. Angle ($\beta$) may be the same as or different than angle ($\alpha$). Assuming angle ($\beta$) is the same as angle ($\alpha$), then the prism 150 does not have any internal reflection. If, however, angle ($\beta$) is different than angle ($\alpha$), then the prism 150 internal reflects the beam 124" within the prism 150. As such, angle ($\beta$) can be between 0 and 90 degrees.

Beam 138 exits prism 150 at hypotenuse face 158 at an angle ($\gamma$) with respect to normal axis line 158N. Angle ($\gamma$) may be zero degrees, thereby indicating that beam 138 exits hypotenuse surface 158 along normal axis line 158N. Alternatively, the beam 138 may be exit at an angle ($\gamma$) offset from normal axis line 158N. The angle ($\gamma$) may be from about 1 degrees to about 89 degrees, and potentially from about 15 degrees to about 85 degrees, and possibly from about 30 degrees to about 75 degrees, and conceivably from about 45 degrees to about 65 degrees, and even 55 degrees to about 65 degrees, and maybe even about 60 degrees to about 65 degrees, and possibly even about 60 degrees or about 59.416 degrees.

Refraction of the beam passing through the prism 150 affects beam characteristics, which include at least one of beam size, beam width, beam height, beam aspect ratio, beam long axis, and beam divergence. As mentioned above, laser beams 124" entering the prism 150 at surface 152 has a first aspect ratio. It may be desirable for the laser beam 138 exiting the hypotenuse surface 158 to have a second aspect ratio. The second aspect ratio may be calculated as the ratio of a second beam width ($w_2$) to a second beam height ($h_2$) and may be written as $w_2$:$h_2$. Laser beam 138 may be rectangular in cross-section and have a second beam width ($w_2$) and a second beam height ($h_2$).

In embodiments, the second width $w_2$ may be less than, equal to or greater than the first width $w_1$. The second height $h_2$ may be less than, equal to or greater than the first height $h_1$. The second aspect ratio may be less than, equal to or greater than the first aspect ratio. The aspect ratio of beam 138 is optically tailored via prism 150 to alter the laser generator system's beam characteristics (i.e., those of laser beam 124) to generate beam 138 suitable for coupling to disposable fiber optic catheters at fiber coupler 142. For example, the first aspect ratio for beam 124 (124', 124") may be about 2.22:1.00 and the second aspect ratio for beam 138 may be about 1.45:1.00. Prism variables effecting output includes the angle of incidence entering bottom surface 152, the angle ($\phi$) of the prism, index of refraction of the prism material, and wavelength of laser input.

Further depicted in FIG. 5A, optical assembly 120 may include a safety shutter 144. Shutter 144 may be disposed anywhere along optical pathway 126 between laser source 122 and coupler 142 in order to provide a means for interrupting the laser beam and prevent said beam from being delivered to the coupler 142. For example, shutter 144 may be positioned between prism 150 and plano-convex lens 140 as shown in FIG. 5A. In normal operation of laser generator 100, safety shutter 144 is open to allow beam 138 to pass from prism 150 to plano-convex lens 140 unhindered. Laser generator 100 having optional shutter 144 provides a fail-safe mechanism to limit laser beam delivery to the patient as needed. Safety shutter 144 may be closed via a microprocessor executable controller upon receipt of a fault signal. A fault signal may be generated if at least one of the first energy as measured for beam 128 and/or the second energy as measured for beam 129 is determined to be outside of an acceptable energy for delivery to a patient.

Figure 6:
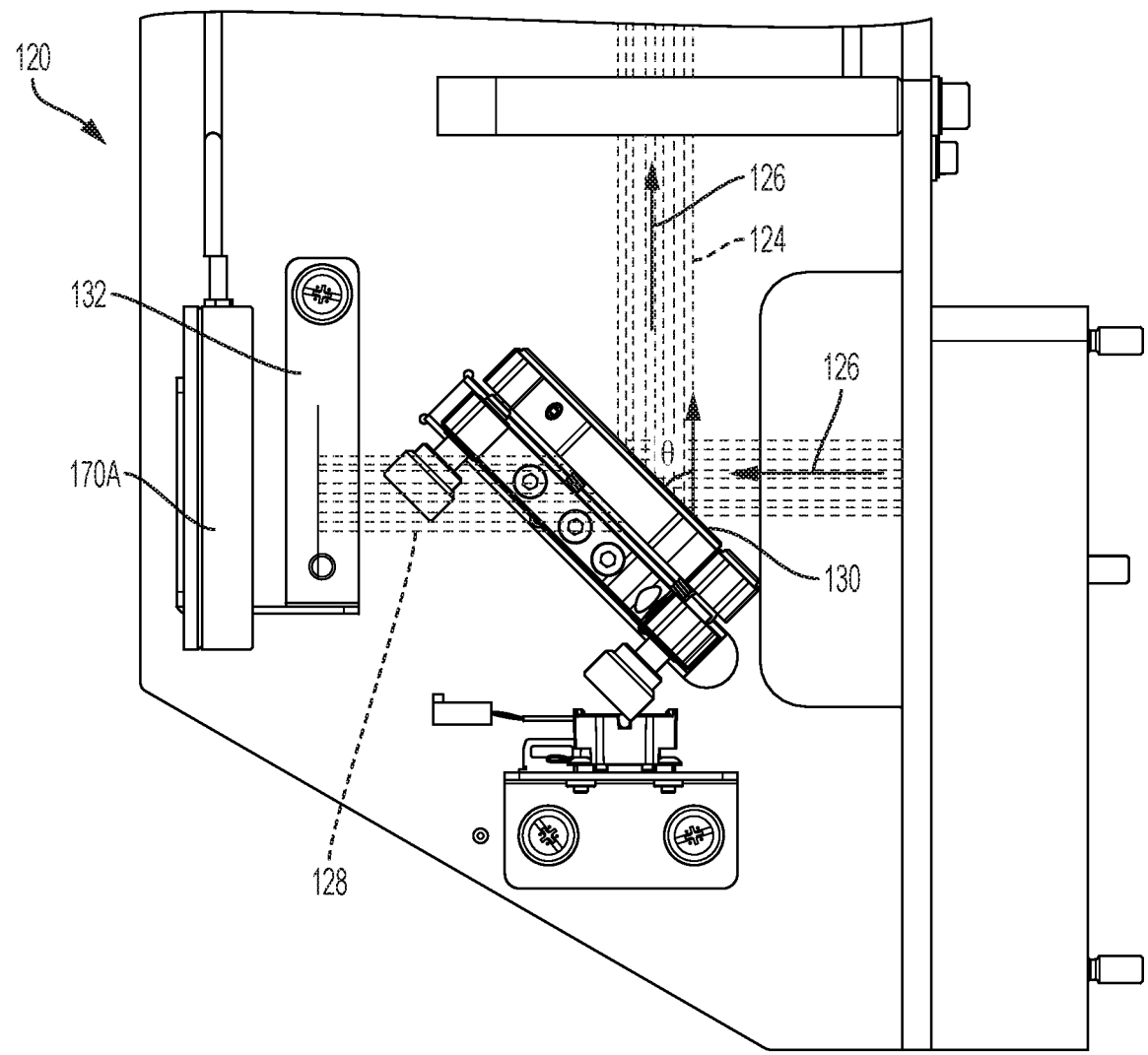
FIG. 6 is an enlarged side view of the mirror and vessel energy sensor of the optical assembly depicted in FIG. 3.

Memory 540 and instructions 550 to controller 520 may be programmed or set according to patient safety and needs. Laser generator 100 may include sensors as discussed. In addition to sensor 136 of FIG. 5A, FIG. 6 depicts an enlarged side view of vessel energy sensor 132 of the optical assembly 120 depicted in FIG. 3. Vessel energy sensor 132 determines first energy as measured for beam 128 as transmitted through side view of mirror as shown in FIG. 6. Prism energy sensor 136 determines second energy as measured for beam 129 as reflected from coating 162 as shown in FIG. 5A. Referring to FIG. 6, mirror 130 may be oriented at an angle (θ) with respect to optical pathway 126. The angle (θ) may be between 0 degrees and 90 degrees including any increment there between. In embodiments, angle (θ) is about 45 degrees. Sensors 132 and 136 measure first and second energy densities, respectively, and provide information to a microprocessor executable controller via components 170A and 170B, for example.

Figure 7A:
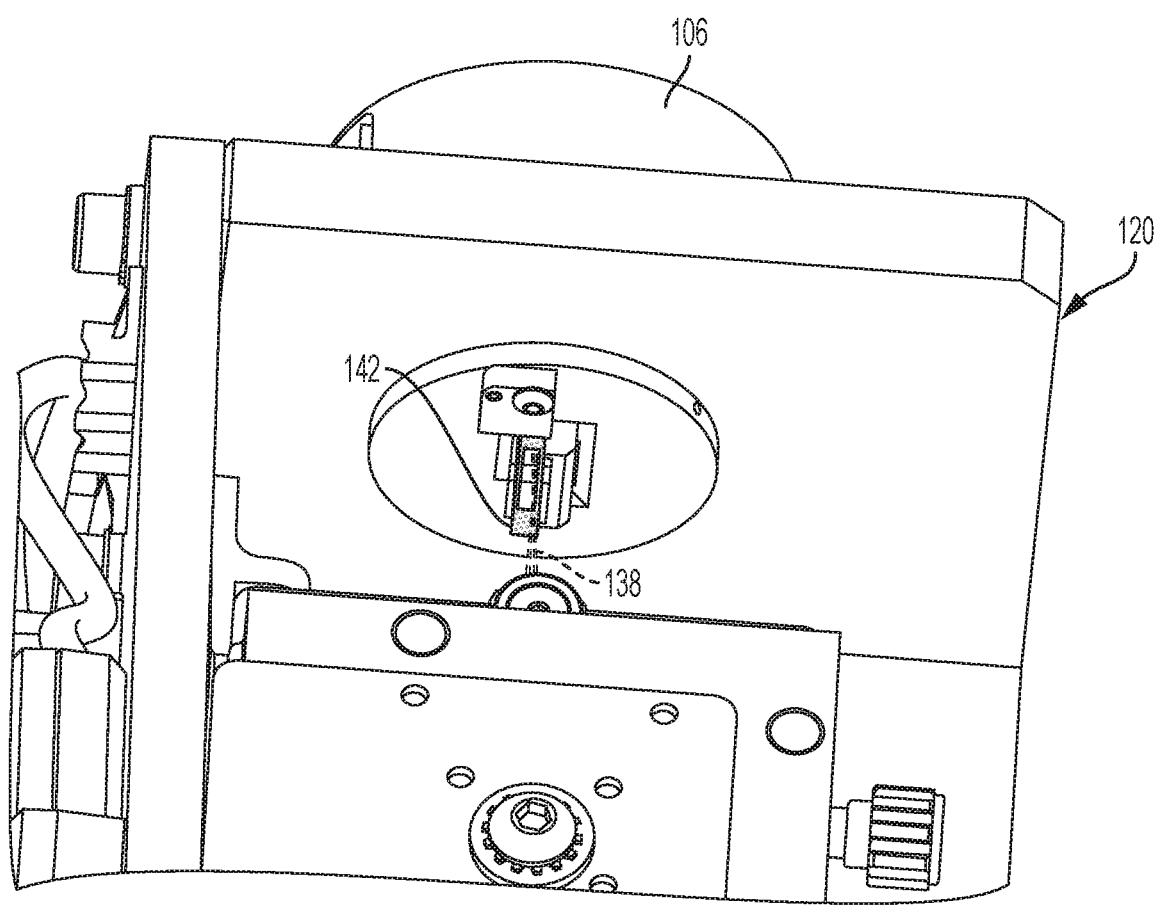
FIG. 7A is a perspective view of the rectangular fiber coupler of the optical assembly depicted in FIG. 3.
Figure 7B:
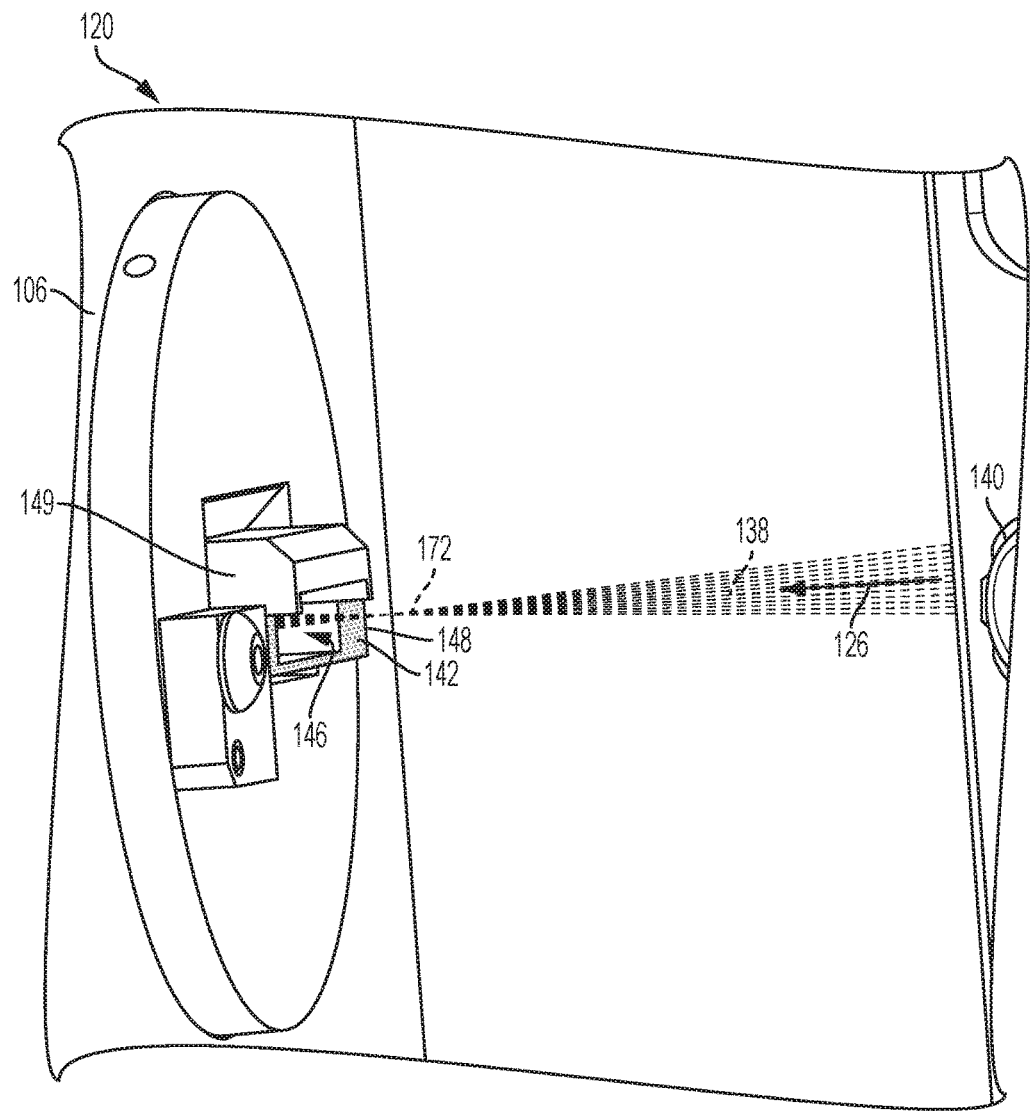
FIG. 7B is another perspective view of the laser beam path to the rectangular fiber coupler depicted in FIG. 7A.
Figure 7C:
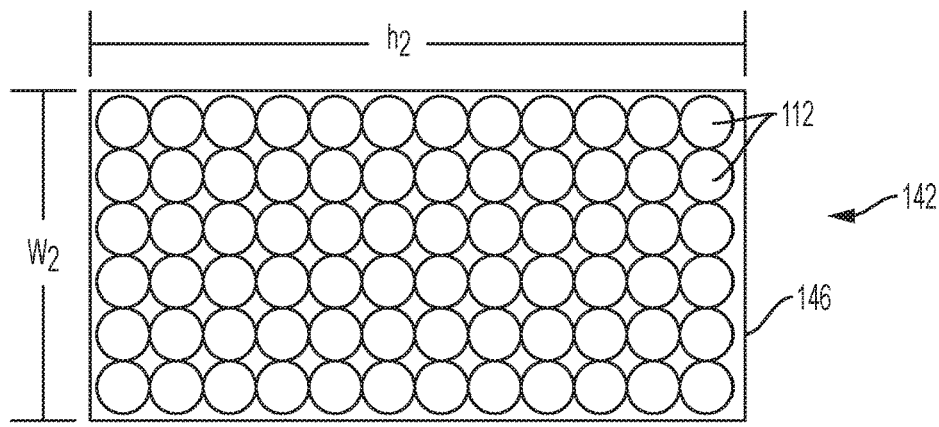
FIG. 7C is a view into the channel of the rectangular fiber coupler of FIG. 7B toward optical fiber ends.

FIG. 7A depicts a perspective view of the laser beam 138 directed to a rectangular fiber coupler 142 of the optical assembly 120 depicted in FIG. 3. Rectangular fiber coupler 142 is coupled to catheter coupler 106. FIG. 7B depicts a perspective view of the laser beam 138 directed to the rectangular fiber coupler 142 as shown in FIG. 7A. The rectangular fiber coupler 142 is disposed distally relative to the point of convergence or focal point 172. The rectangular fiber coupler 142 may comprise a slide mount, which has a channel 146 that is adapted to receive optical fibers (not shown). The channel extends from a point at or adjacent to the proximal end 148 of the slide mount to a distal end of the slide mount. The proximal end of the slide mount is sized and configured to receive the laser beam 138 and the distal end of the slide mount, recess from view distally in FIG. 7B, is sized and configured to transmit light to the optical fibers. The coupler may also include a claim 149 that is mounted on the slide mount adjacent to its proximal end. Channel 146 is rectangular and matches the size and aspect ratio of beam 138, having $w_2$, $h_2$, and an aspect ratio different than beam 124, in the plane including the optical fiber ends 170, as depicted in FIG. 7C. FIG. 7C is a view into the channel 146 from the direction of optical pathway 126.

Figure 7D:
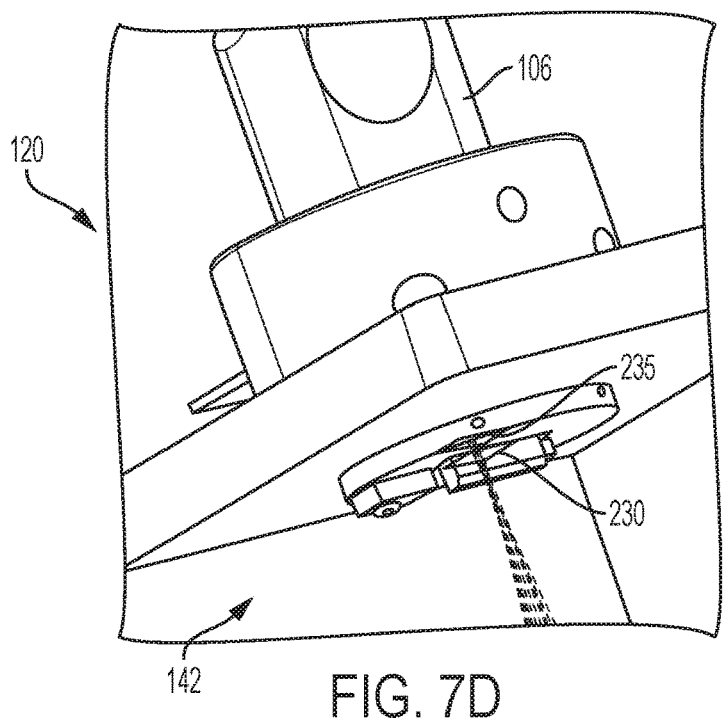
FIG. 7D is an angled side view of the coupler of FIG. 7B illustrating the coupling plane(s) of the beam envelope at the catheter coupler.
Figure 7E:
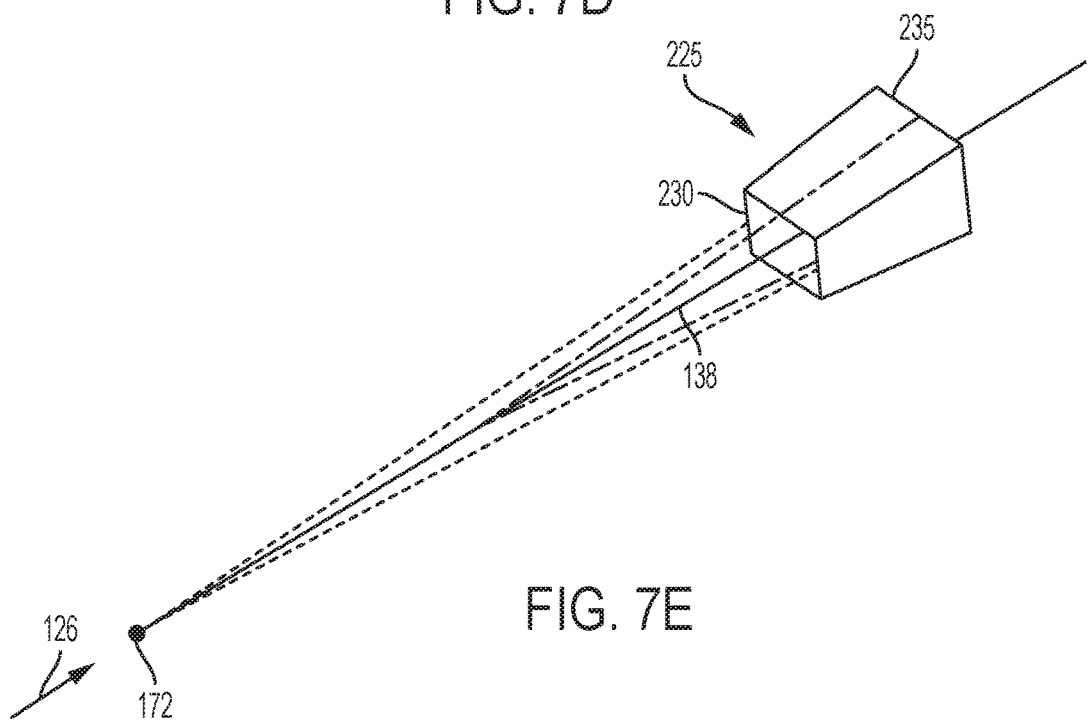
FIG. 7E schematically illustrates the beam envelope having the coupling planes as shown in FIG. 7D.
Figure 7F:
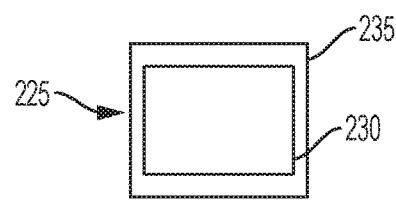
FIG. 7F shows a cross-sectional representation of the coupling planes as shown in FIG. 7D.

FIG. 7D depicts an angled side view of the optical assembly having coupler 142 to show the beam envelope 225 at the catheter coupler as shown schematically in FIG. 7E. The coupler includes multiple coupling planes to accommodate different size fibers. For example, the coupler may include two coupling planes-a first coupling plane 230 at a first distance from the plano-convex lens and a second coupling plane 235 at a second distance from the plano-convex lens 235. Referring to FIG. 7B, plano-convex lens 140 is a distance from focal point 172. Coupling planes 230 and 235 lie extended at first and second distances, respectively, further from focal point 172 relative to lens 140. The combination of the prism 150 and the plano-convex lens 140 changes beam 138 affecting beam divergence as well as aspect ratio. In other words, the optical assembly 120 having lens 140 and prism 150 alters beam 138 so that at coupling plane 230 the beam (138A) has a third aspect ratio and at coupling plane 235 the beam (138B) has a fourth aspect ratio. Therefore, so that the first coupling plane has a third aspect ratio and the second coupling plane has a fourth aspect ratio. Coupling plans 230 and 235 are shown in cross-section in FIG. 7F.

FIG. 8 is a functional block diagram depicting an illustrative system 500, in accordance with embodiments of the subject matter disclosed herein. As shown, the laser generator system 500 may include a laser source 122 and an optical assembly 120 as described herein. In embodiments, system 500 may be, be similar to, include, or be included within device 100 (and/or any of its components) depicted in FIG. 1A and/or the device 104 (and/or any of its components) depicted in FIG. 1B. In embodiments, assembly 120 may be similar to, include, or be included within device and/or assembly 120 (and/or any of its components) depicted in FIGS. 2-7C. The system 500 may further include microprocessor executable controller 520 configured to obtain feedback from optical assembly components, such as components 170A and 170B, coupled to sensors 132 and 136, respectively, as shown in FIG. 3. System 500 also includes input and/or output ports and/or components 510 and power supply 530 for the laser source 122.

Generally, controller 520 may include one or more processors 560, memory 540 and one or more modules that contain logic or instructions 550 stored in memory 540 for controlling the operation of the system 500. For example, upon a clinician activating footswitch 108, the footswitch 108 creates and sends a signal to the controller 520, which in turn allows the flow of current from the power supply 530 to the laser source 122 and activates the laser generator, which sends a laser beam along the optical path in the optical assembly 120, which in turn provides a laser beam to the catheter 106. Controller 520 may include any type of computing device suitable for implementing aspects of embodiments of the disclosed subject matter. Examples of computing devices include specialized computing devices or general-purpose computing devices such "workstations," "servers," "laptops," "desktops," "tablet computers," "handheld devices," "smartphones," "general-purpose graphics processing units (GPGPUs)," and the like, all of which are contemplated within the scope of FIG. 8.

In embodiments, the controller 520 may include a bus (not shown) that, directly and/or indirectly, couples the following devices: an input/output (I/O) port and/or components 510, a power supply 530, a processor 560, and a memory 540 including instructions 550. Any number of additional components, different components, and/or combinations of components may also be included in the controller 520 or system 500. Feedback, such as in the form of signals, provided to controller 520 from footswitch 108, sensor 132 and/or sensor 136 is utilized by the processor 560 having instructions 550 stored in memory 540 to activate the laser source 122, attenuator 134 and/or shutter 144 as needed. For example, the sensor 132 measures the energy of the laser beam exiting the laser source 122, and the sensor 136 measures the energy of the laser beam entering and/or exiting the prism 150 prior to the laser beam entering the plano-convex focusing lens 140. And it may be desirable for the controller 520 to adjust the power supply 530 (or laser source 122) and/or the attenuator 134 to modify the energy of the laser beam exiting the laser source 122 and the energy of the laser beam entering and/or exiting the prism 150, respectively.

Input/output ports and/or components 510 of system 500 provide interactive means for the clinician to select appropriate settings for operation of system 500 having controller 520. One setting that the clinician may choose includes appropriate setting for beam density (or fluence) to be delivered to the patient based upon the medical procedure for the patient. The system 500 may include a component 510, such as a density (or fluence) button or selector that allows the clinician to adjust the output energy of the system 500. The fluence value (in $mJ/mm^2$) is increased or decreased by depressing the appropriate button selector switch. For example, the energy (or fluence) button or selector may allow the clinician to adjust and set the output energy of the system 500 to one or more of a plurality of settings. Similarly, the system 500 may include a separate component in the form of a pulse rate button or selector that allows the clinician to adjust the pulse rate (pulses/second) of the laser beam emitted by the source 122. Upon the controller 520 (including the processor 560) receiving an activation signal (an "on" signal) from the foot switch 108, the laser source 122 and system 500 produce a laser beam, which travels through the optical assembly 120 and is emitted by the laser catheter 106. Similarly, upon the controller 520 (including the processor 560) discontinuing to receive an activation signal (an "on" signal) from the foot switch 108 or upon the controller 520 (including the processor 560) receiving a deactivation signal (an "off" signal) from the foot switch 108, the laser source 122 and system 500 discontinues producing a laser beam.

Selection of the catheter is performed by the clinician according to the procedure/therapy to be delivered. According to the catheter selected, the laser has a prescribed target energy (fluence) and pulse rate as well as a range over which these parameters can be varied. Alternatively, a clinician may be able to adjust the output energy of the system 500 by selecting a corresponding position for density (or fluence) button or selector. Beam energy may be then determined at sensors 132 and/or 136, the values of which are communicated to controller 520 via components 170A and 170B or other. Depending upon the clinician's initial selection, the controller 520 sends a signal to the power supply 530 and the laser source 122 to produce the corresponding amount of power and laser energy. The sensor 132 determines the energy produced and emitted in form of a beam from the laser source 122, and the sensor 136 determines the energy of the beam after the beam is refracted by the prism 150 and transmitted to the coupler. Based upon the instructions, the selection switch position or setting signal, the measurements of the energy from the sensors 132 and 136, the controller may send a signal to the attenuator 134 thereby causing the attenuator 134 to rotating the louvers of the attenuator 134 and affect beam density. Depending upon the instructions and input signals, the attenuator 134 may increase beam intensity, decrease beam intensity or leave beam intensity the same.

Calibration of the laser depends on the selected catheter and utilizes sensor 137. The calibration process determines the ratio between sensor 136 and sensor 137 over the energy range prescribed according to the catheter (as selected by the clinician). This is done so that once the catheter is in vivo and its energy output no longer directly measured, the energy at sensor 136 can be used to infer the energy being directed out the distal end of the catheter.

Selection of the desired catheter energy is accomplished by depressing the appropriate button selector switch 510. Upon selection of the desired energy, the controller 520 will determine the appropriate laser source energy 122 and attenuator 134 to achieve the desired energy optimized such that the minimum laser source 122 energy is utilized.

Delivery of selected energy is actuated upon activating footswitch 108 causing laser source 122 and system 500 to produce a pulsed laser beam. The energy at sensor 136 is monitored upon generation of each pulse and is processed by the controller 520 according to a servo control algorithm such that the energy is maintained at the prescribed level. If necessary, the controller 520 will adjust the laser energy source 122 to obtain the desired energy. If a more coarse adjustment is required the attenuator 134 can also be adjusted. In this way the controller 520 continually monitors and adjusts the laser energy source 122 and attenuator 134 such that the minimum laser source 122 energy is maintained.

Shutter 144 is initialized to a CLOSED position upon system 500 power-up. Shutter 144 opens when the controller 520 begins to process a transition from READY to FIRING (i.e. when the footswitch 108 is activated.) Based upon instructions 550, a fault signal may be generated thereby directing the controller to provide a signal to the shutter 144 to close it and prevent the beam from reaching the optical fiber. A fault signal may be generated as follows: (i) when the controller 520 begins to process a transition from FIRING to READY (i.e. when the footswitch 108 is deactivated); (ii) when the energy read at sensor 136 subsequent to a pulse being generated that exceeds the desired pulse energy by a safety margin; and (iii) when the controller 520 determines an exception has occurred that might compromise the ability of system 500 to control pulse laser energy.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A laser generator comprising:
   a laser source producing a first beam of light having a first aspect ratio;
   an optical assembly comprising:
   a prism having:
   a surface configured to receive the first beam at an incoming angle of incidence relative to a first surface normal; and
   an additional surface configured to transmit, at an exit angle relative to a second surface normal, a second beam having a second aspect ratio;
   a lens disposed between the prism and the coupler, wherein the lens is configured to converge the second beam and transmit the second beam to the coupler,
   wherein the coupler comprises:
   a first coupling plane at a first distance from the lens;
   a second coupling plane at a second distance from the lens; and
   wherein the combination of the prism and the lens is configured to converge the second beam to a focal point between the lens and the coupler such that the second beam diverges between the focal point and the coupler, wherein the second beam comprises a third aspect ratio at the first coupling plane and comprises a fourth aspect ratio at the second coupling plane,
wherein the first aspect ratio, second aspect ratio, third aspect ratio, and fourth aspect ratio are different from one another.

2. The laser generator of claim 1, wherein the prism is a wedge prism.

3. The laser generator of claim 2, wherein the wedge prism is a right angle wedge prism.

4. The laser generator of claim 1, wherein the optical assembly further comprises a first sensor and a mirror disposed at an angle between the laser source and the prism, wherein the mirror reflects the first beam onto the prism, wherein the mirror further transmits at least a portion of the first beam to the first sensor, the first sensor configured to measure a first energy of the first beam, wherein the mirror transmits about one percent of the first beam to the first sensor.

5. The laser generator of claim 4, further comprising a second sensor configured to measure a second energy of the second beam.

6. The laser generator of claim 5, wherein the additional surface of the prism includes a coating configured to reflect at least a portion of the second beam to the second sensor.

7. The laser generator of claim 6, wherein the coating reflects about two percent of the second beam to the second sensor.

8. The laser generator of claim 7, further comprising a third sensor configured to calibrate the laser source to a selected catheter, the catheter coupled to the optical assembly via the coupler.

9. The laser generator of claim 1, further comprising a microprocessor executable controller and a safety shutter, wherein the safety shutter is disposed between the prism and the lens, wherein the microprocessor executable controller closes the safety shutter upon receipt of a fault signal.

10. The laser generator of claim 1, wherein the prism comprises fused silica.

11. The laser generator of claim 1, wherein the optical assembly further comprises an attenuator disposed between the laser source and the prism, wherein the attenuator is configured to adjust the first energy of the first beam.

12. The laser generator of claim 11, further comprising a microprocessor executable controller coupled to the attenuator, wherein the microprocessor executable controller adjusts the first energy of the first beam measured by a first sensor with the attenuator based upon the second energy of the second beam measured by a second sensor.

13. The laser generator of claim 12, wherein the microprocessor executable controller adjusts the first energy of the first beam with the attenuator based upon the second energy of the second beam measured by the second sensor and the first energy of the first beam measured by the first sensor.

14. The laser generator of claim 13, wherein the optical assembly further comprises a mirror that reflects the first beam onto the prism, wherein the mirror further transmits at least a portion of the first beam to the first sensor.

15. The laser generator of claim 1, wherein the prism comprises a bottom surface, and the surface configured to receive the first beam is the bottom surface.

16. The laser generator of claim 1, wherein the prism comprises a hypotenuse surface, and the additional surface is the hypotenuse surface.

17. The laser generator of claim 1, wherein lens is a plano-convex lens.

18. The laser generator of claim 1, wherein the prism comprises:
a bottom incident face configured to receive the first beam at an angle of 15 to 30 degrees off normal to the bottom incident face, the first beam having a first width and a first height;
a side face connected to the bottom incident face by an edge at an angle of 90 degrees; and
a hypotenuse exit face connecting the bottom incident face and the side face, the hypotenuse exit face configured to emit the second beam at an angle of 50 to 70 degrees off normal to the hypotenuse exit face, the second beam having a second width and a second height, wherein the second width is less than the first width, and wherein the second height is the same or equal to the first height.

19. The laser generator of claim 1, wherein the prism is configured to receive the first beam along an optical path and to affect at least one of:
beam size;
beam divergence;
beam long axis; and
beam aspect ratio.

20. A system comprising:
a laser generator comprising:
a laser source producing a first beam of light;
an optical assembly comprising:
a prism having:
a surface configured to receive the first beam at an incoming angle of incidence relative to a first surface normal; and
an additional surface configured to transmit, at an exit angle relative to a second surface normal, a second beam having a second aspect ratio;
a coupler; and
a lens disposed between the prism and the coupler, wherein the lens is configured to transmit the second beam to a coupler;
wherein the coupler comprises:
a first coupling plane at a first distance from the lens; and
a second coupling plane at a second distance from the lens;
wherein the combination of the prism and the lens is configured to converge the second beam to a focal point between the lens and the coupler such that the second beam diverges between the focal point and the coupler, wherein the second beam comprises a third aspect ratio at the first coupling plane and comprises a fourth aspect ratio at the second coupling plane,
wherein the first aspect ratio, second aspect ratio, third aspect ratio, and fourth aspect ratio are different from one another; and
a catheter comprising a plurality of optical fibers, wherein the catheter comprises a proximal end and a distal end, wherein the proximal end is coupled to the coupler of the laser generator.

* * * * *